United States Patent

Caciagli

Patent Number: 5,112,996
Date of Patent: May 12, 1992

[54] METHOD FOR ALKYLATING GUANIDINO GROUPS

[75] Inventor: Valerio Caciagli, Rome, Italy

[73] Assignee: Sclavo S.p.A., Siena, Italy

[21] Appl. No.: 573,812

[22] Filed: Aug. 28, 1990

[30] Foreign Application Priority Data

Sep. 4, 1989 [IT] Italy .................... 21612 A/89

[51] Int. Cl.$^5$ .......................... C07C 271/22
[52] U.S. Cl. ................................. 552/104
[58] Field of Search ........................ 552/104

[56] References Cited

U.S. PATENT DOCUMENTS 4,041,156 8/1977 Okamoto et al. ............... 552/104

Primary Examiner—C. Warren Ivy
Assistant Examiner—Raymond Covington
Attorney, Agent, or Firm—Birch, Stewart, Kolasch & Birch

[57] ABSTRACT

A method is described for substituting at least one hydrogen atom originally present in the guanidino group of a compound of general formula (I)

$$R-NH-\underset{\underset{NH}{\|}}{C}-NH_2 \qquad (I)$$

where R is any substituted or unsubstituted residue, by a group $R_1$ where $R_1$ is an unsubstituted or substituted, linear or branched alkyl, consisting of:

a) silylating the guanidino group and any other silylatable functional groups present within the R group and b) alkylating the product obtained in step a) with a mixture consisting of the alkyl halide $R_1$-X and an organic base containing a tertiary nitrogen.

11 Claims, No Drawings

METHOD FOR ALKYLATING GUANIDINO GROUPS

This invention relates to a new method for alkylating guanidino groups. More specifically, the invention relates to a method for the N-alkylation of guanidine compounds of general formula (I)

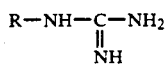

where R is any substituted or unsubstituted residue in which any easily alkylatable groups can be suitably protected.

For the purposes of the present invention the term "alkylation" of the guanidino group means the substitution of at least one hydrogen atom originally present in the guanidino grouping $-NH-C(=NH)-NH_2$ by a group $R_1$ where $R_1$ is an unsubstituted or substituted, linear or branched alkyl group.

The term "substituted alkyl group" means an alkyl radical which carries one or more substituents, independently chosen from aryl, heteroaryl, cycloalkyl, halogen, alkoxy, aryl-thio, heteroaryl-thio etc.

Guanidino groups are generally alkylated by hot-reacting the guanidine compound to be alkylated with the desired alkyl halide (preferably the iodide) or tosylate of formula $R_1-X$ where X is the halide or tosylate anion and $R_1$ is a possibly substituted alkyl group [see P. A. Smith—The Chemistry of Open-Chain Organic Nitrogen Compounds—Volume 1, pages 233-290—(1965)]. The reaction is typically conducted in aqueous solution made basic by adding an alkaline hydroxide, and in some cases, particularly those in which the $R_1$ group is a tertiary group, the reaction yield is extremely low because of the instability of the reagent $R_1-X$ in the aqueous solution. In these cases the alcohol $R_1-OH$ forms.

It has now been found possible to conduct the alkylation of a guanidino group of a compound of formula (I) in an aprotic organic solvent by a process comprising the following steps:
a) silylating the guanidino group and any other silylatable functional groups within the R group by using an N,O-bis(tri-alkyl-silyl)acetamide possibly mixed with a tri-alkyl-silyl chloride and, in this latter case, in the presence of an organic base containing a tertiary nitrogen, not necessarily suitable for the deprotonation of the guanidino group;
b) alkylating using a mixture consisting of the alkyl halide $R_1-X$ and an organic base containing a tertiary nitrogen, also not necessarily suitable for the deprotonation of the guanidino group.

The reaction is conducted in the presence of any aprotic inert solvent such as an alkyl or cyclic ether, e.g. diethyl ether, diisopropyl ether, dioxane, tetrahydrofuran, dimethoxyethane etc, a halogenated alkyl or aryl hydrocarbon such as methylene chloride, chloroform, dichloroethane, chlorobenzene etc., or a mixture thereof.

If as silylating agent only an N,O-bis(tri-alkyl-silyl)acetamide such as trimethyl-silylacetamide or triethyl-silylacetamide is used in the silylating step a), this is used in a quantity at least equimolar with the compound of formula (I) and preferably in an excess over this quantity. Typically, the acetamide derivative is used in a quantity of between 1 and 2.5 moles per mole of the compound of formula (I).

However, according to a preferred aspect of the present invention, if a mixture of a tri-alkyl-silyl chloride such as trimethylsilyl chloride or triethylsilyl chloride and an N,O-bis(tri-alkylsilyl)-acetamide is used, these two silylating agents are used in respective quantities of between 0.5 and 1.5 and between 1 and 2 moles per mole of the guanidine compound to be alkylated. Generally, the optimum molar ratio between these respective silylating agents and the guanidine compound varies between 0.75 and 1.2 and between 1.25 and 1.75 respectively.

Obviously if the compound of formula (I) contains other trialkylsilylatable groups in addition to the guanidino group itself, the molar quantity of silylating agent or agents must be increased. The aforesaid ratios can be considered to substantially relate to each silylatable group in the starting compound.

If a tri-alkyl-silyl chloride is used in addition to the N,O-bis(tri-alkyl-silyl)acetamide, the reaction is preferably conducted in the presence of an organic base containing a tertiary nitrogen, although this need not be suitable for deprotonating the guanidino group. Organic bases which can be advantageously used in this step are the tri-alkyl-amines, and in particular triethylamine (TEA) and diisopropyl-ethylamine, pyridine and alkyl-pyridines such as picolines, lutidines etc. This organic base is used in a quantity at least equimolar with the tri-alkyl-silyl chloride used, but is preferably used in excess, typically in an excess of up to 50 mol % over the tri-alkyl-silyl chloride.

The reaction can be conveniently conducted at ambient temperature, even though generally it is preferable to heat to reflux temperature to optimize the progress.

Once silylation of the initial guanidine compound by the tri-alkylsilyl derivative in the chosen solvent has been accomplished, the guanidino group is alkylated in accordance with step b). The alkylation reaction is effected by adding to the solution deriving from step a) a quantity of alkyl halide $R_1-X$ at least equal to the stoichiometric reaction quantity but preferably an excess, and an organic base containing a tertiary nitrogen, not necessarily suitable for deprotonating the guanidino group, in a quantity at least equimolar with the alkyl halide.

If a mono-alkylated product is required, the alkyl halide $R_1-X$ is preferably used in slight excess over the stoichiometric (5-10 mol %), whereas if a more substituted product is desired it is preferable to operate with a strong excess of alkyl halide.

The alkylation reaction is generally complete in 24-48 hours. This step can also be conducted at ambient temperature but is preferably conducted at a temperature higher than ambient, and typically at reflux temperature.

On termination of the reaction mild acidification is carried out and the desired product is then recovered from the reaction mixture by conventional isolation and purification techniques. If desired, the crude product obtained can be further purified by distillation or chromatography.

As stated, the initial guanidine compound of formula (I) can contain other easily alkylatable groups. In this case, if these are not to be alkylated either they must be protected before alkylating the guanidino group, or alternatively when the product substituted both at the guanidino group and at the alkylatable functional group has been obtained this latter group must be selectively removed.

The reaction is substantially of general application and can be adapted to the alkylation of any guanidine compound of formula (I).

It is however of particular interest in the alkylation of guanidine compounds of formula (I) in which R is an alkyl group substituted with one or more groups independently chosen from amino, mono- and di-alkyl-amino, mono- and di-aryl-amino, phenyl, substituted phenyl, heteroaryl, substituted heteroaryl, carboxy, carbalkoxy and carbamyl.

In this respect, if starting compounds of formula (I) are used in which R is thus defined, derivatives of arginine and of the gem-diamino or malonyl analogues of arginine protected in the side chain by a suitably chosen alkyl group can be obtained, these being useful in the synthesis of peptides and retro-inverso peptides containing one or more "Arg" or "g-Arg" or "m-Arg" units; or guanidine derivatives useful in the cardiovascular field as described in WO-A-8707891 and in DE-A-3631334. If, according to a preferred aspect of the present invention, the alkylation is conducted on a guanidine compound chosen from arginine and the gem-diamino or malonyl analogues of arginine, in order to introduce a protecting group for the guanidino function in the side chain, the alkylation is conducted with an alkylating agent $R_1-X$ where $R_1$ is an alkyl group as heretofore defined, which is easily removable under conditions which do not alter the structure of the thus synthesized peptide. A typical example of an alkyl group which can act as a good protector group is the trityl or substituted trityl group. To obtain alkylation only in the side chain, in the case of arginine or the corresponding gem-diamino derivative, either the α-amino groups must be protected before the tri-alkylsilylation step or an excess of the alkylating agent $R_1-X$ must be used, with subsequent selective removal of the $R_1$ group from the α-amino groups by forming the hydrochloride and treating this with methanol or by direct treatment with hot acetic acid. As stated, with regard to the quantity of silylating agent to be used in step a), it must be considered that both the carboxyl group and the amino group are groups which are easily silylatable.

If starting with a pure isomer of arginine, the process of the invention can lead to a small percentage of racemization, depending on the chosen reaction conditions.

If necessary the final product can be separated into its isomers by conventional methods, such as by chiral column chromatography or by the formation of a salt with an asymmetric base and fractional crystallization of the two diastereoisomers.

If it is desired to obtain the compounds described in DE-A-3631334 or WO-A-8707891, an imidazolyl-alkyl halide suitably protected at the imidazole nitrogen is used as alkylating agent.

The following example describes one embodiment of the method of the present invention in detail, but must not be considered as limitative of the scope thereof.

EXAMPLE $N^G$-trityl-arginine and $N^G$-ditrityl-arginine

A mixture of arginine (1.77 g, 10 mmoles) and trimethylchloro-silane (TMSC) (1.26 ml, 10 mmoles) in methylene chloride (30 ml) is heated under reflux for 30 minutes. Diisopropylethylamine (DIPEA) (1,59 ml, 10 mmoles) is then added and the mixture again heated under reflux for 30 minutes, after which N,O-bis(-trimethyl-silyl)acetamide (BSA) (4.8 ml, 20 mmoles) is added and heating under reflux continued for a further 30 minutes until a homogeneous solution is obtained, to which commercial trityl chloride (TrtCl) (2.78 g, 10 mmoles) are added and heating under reflux continued for 30 minutes.

BSA (10 ml, 40.9 mmoles). DIPEA (10 ml. 5.8 mmoles) and commercial TrtCl (2.78 g, 10 mmoles) are then added to this reaction mixture and the mixture obtained is kept heated under reflux. After 20 hours of reaction further trityl chloride (2.78 g, 10 mmoles) is added and heating under reflux continued for a further 28 hours.

After cooling to ambient temperature, the mixture is acidified with a ⅛ (v/v) acetic acid/methylene chloride mixture. Ethyl ether is then added to the resultant organic phase until it is lighter than water, after which it is washed abundantly with water (6×100 ml), with an aqueous 5% NaHCO₃ solution (50 ml) and again with water (2×50 ml). The organic phase is dried with Na₂SO₄, filtered and evaporated to dryness in a rotary evaporator, to obtain a spongy yellow solid. This crude product is dissolved in AcOH (50 ml) and maintained at 50° C. for 1 hour, after which the AcOH is evaporated under 1 mm Hg and the residue taken up and evaporated several times in toluene (until all the AcOH has been removed).

The residue is taken up in 30 ml of Et₂O added drop by drop under strong stirring. The crude precipitate obtained in this manner (3.6 g) is subjected to reverse phase HPLC [Column Lichosorb RP18 (10μ) (25×0.4 cm); Eluent: A=CH₃CH, 0.1% TFA; B=H₂O, 0.1% TFA; gradient: from 37 to 80% of A in B in 20 minutes; Flow: 1.5 ml/min] and found to contain two compounds with a retention time of 3.89 and 14.55 minutes). The first compound, which represents the major part of the mixture, coelutes with an authentic sample of $N^a$—Trt—Arg—OH, whereas the second compound coelutes with an authentic sample of $N^a$—(Trt)₂—Arg—OH.

I claim:

1. A method for substituting at least one hydrogen atom originally present in the guanidino group of a compound of the formula (I)

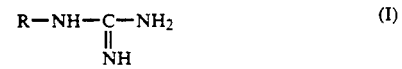

wherein R is any substituted or unsubstituted hydrocarbon residue, by a group $R_1$ wherein $R_1$ is an unsubstituted or substituted trityl group, comprising:

a) silylating the guanidino group and other silylatable functional groups possibly present within the R group by treating the guanidine compound of formula (I) in an aprotic organic solvent with an N,O-bis(tri-alkyl-silyl)acetamide alone or optionally mixed with a tri-alkyl-silyl chloride and an organic base containing a tertiary nitrogen; and b) alkylating the product obtained in step a) with a mixture consisting of an optionally substituted trityl halide $R_1-X$ wherein X is a halide anion, and an organic base containing a tertiary nitrogen.

2. The method of claim 1, wherein $R_1$ is a trityl group which can carry one or more substituents, independently chosen from the group consisting of halogen, and alkoxy.

3. The method of claim 1, wherein R is an alkyl group substituted with one or more groups independently chosen from amino, mono- and di-alkyl-amino, mono- and di-aryl-amino, phenyl, substituted phenyl, heteroaryl, substituted heteroaryl, carboxy, carbalkoxy and carbamyl.

4. The method of claim 1, wherein the aprotic organic solvent is chosen from alkyl or cyclic ethers, halogenated alkyl or aryl hydrocarbons, and mixtures thereof.

5. The method of claim 1, wherein in step a) an N,O-bis(tri-alkyl-silyl)acetamide chosen from trimethylsilylacetamide and triethylsilylacetamide is used as the silylating agent, in a quantity at least equimolar with the compound of formula (I).

6. The method of claim 5, wherein the N,O-bis(tri-alkyl-silyl)acetamide is used in a quantity of between 1 and 2.5 moles per mole of the compound of formula (I).

7. The method of claim 1, wherein in step a) a mixture of a tri-alkyl-silyl chloride chosen from trimethylsilyl chloride and triethylsilyl chloride and an N,O-bis(tri-alkylsilyl)-acetamide is used in quantities of between 0.5 and 1.5 and between 1 and 2 moles per mole of the starting guanidine compound respectively, in the presence of an organic base containing a tertiary nitrogen in a quantity at least equimolar with the tri-alkyl-silyl chloride.

8. The method of claim 1, wherein the organic base containing a tertiary nitrogen is chosen from tri-alkyl-amines, pyridine and alkyl-pyridines.

9. The method of claim 7, wherein said base is chosen from triethylamine (TEA) and diisopropyl-ethylamine.

10. A method for substituting at least one hydrogen atom originally present in the guanidino group of a compound of the formula (I)

$$R-NH-\underset{\underset{NH}{\|}}{C}-NH_2 \qquad (I)$$

wherein R is any substituted or unsubstituted alkyl residue, by a trityl group, comprising:
   a) silylating the guanidino group and other silylatable functional groups possibly present within the R group by treating the guanidine compound of formula (I) in an aprotic organic solvent with an N,O-bis(tri-alkyl-silyl)acetamide alone or mixed with a tri-alkyl-silyl chloride and an organic base containing a tertiary nitrogen; and
   b) alkylating the product obtained in step a) with a mixture of a trityl halide and an organic base containing a tertiary nitrogen.

11. The method according to claim 10 wherein R is a 4-amino-4-carboxy-butyl radical.

* * * * *